US012691103B2

(12) United States Patent
Yang et al.

(10) Patent No.: US 12,691,103 B2
(45) Date of Patent: Jul. 28, 2026

(54) APPLICATION OF RILUZOLE IN TREATMENT OF OLIGOSPERMIA

(71) Applicant: Jinan University, Guangzhou (CN)

(72) Inventors: Yan Yang, Guangzhou (CN); Yadong Huang, Guangzhou (CN); Rufei Huang, Guangzhou (CN)

(73) Assignee: JINAN UNIVERSITY, Guangzhou (CN)

( * ) Notice: Subject to any disclaimer, the term of this patent is extended or adjusted under 35 U.S.C. 154(b) by 508 days.

(21) Appl. No.: 18/454,796

(22) Filed: Aug. 24, 2023

(65) Prior Publication Data

US 2023/0390253 A1 Dec. 7, 2023

Related U.S. Application Data

(63) Continuation of application No. PCT/CN2023/078695, filed on Feb. 28, 2023.

(30) Foreign Application Priority Data

Mar. 1, 2022 (CN) ........................ 202210192663.2

(51) Int. Cl.

| | |
|---|---|
| *A61K 31/428* | (2006.01) |
| *A61K 45/06* | (2006.01) |
| *A61P 15/08* | (2006.01) |

(52) U.S. Cl.

CPC ............ *A61K 31/428* (2013.01); *A61K 45/06* (2013.01); *A61P 15/08* (2018.01)

(58) Field of Classification Search

CPC ........ A61K 31/428; A61K 45/06; A61P 15/08

See application file for complete search history.

(56) References Cited

U.S. PATENT DOCUMENTS

2002/0019426 A1* 2/2002 Dib ...................... A61K 31/425 514/367

FOREIGN PATENT DOCUMENTS

WO WO-2016140878 A2 * 9/2016 ............ A61K 45/06

* cited by examiner

*Primary Examiner* — Savitha M Rao
*Assistant Examiner* — Elena V Vishnyakova

(57) ABSTRACT

An application of riluzole, a non-hormone compound, in a treatment of oligospermia provides a useful help for solving the problem of male sterility, and has potential application prospects in the field of medicine.

14 Claims, 17 Drawing Sheets

APPLICATION OF RILUZOLE IN TREATMENT OF OLIGOSPERMIA

TECHNICAL FIELD

The disclosure relates to the technical field of pharmacy, and particularly to an application/use of riluzole or a prodrug thereof in treatment of oligospermia.

BACKGROUND

Infertility affects about 15% of couples worldwide, of which about 50% are caused by men. With aggravation of competition pressure in modern society and aggravation of environmental pollution such as radiation, haze and deterioration of water quality, an incidence of male infertility is increasing day by day, which has seriously affected family harmony and quality of life. It is reported that 10-15% of infertile male have an extremely low sperm count in semen, indicating to suffer from severe oligospermia (SO). The oligospermia is one of the most serious forms of male infertility, in which the patient has less than 5 million sperm per milliliter in ejaculation mainly due to the failure of spermatogenesis. Researches have shown that many factors can interfere with the process of spermatogenesis, reduce the quality and quantity of sperm, and thus lead to oligospermia. First of all, testicular injury caused by any reason may cause primary testicular failure and hypogonadism. Damage to testicular structure can lead to interruption of spermatogenesis, cancer therapies such as chemotherapy and radiotherapy can directly destroy the germ cell lineage and damage seminiferous tubule, leading to azoospermia or oligospermia. In addition, busulfan, a chemotherapeutic drug mainly used to treat chronic myeloid leukemia clinically, can produce serious reproductive toxicity during use, causing reproductive disorders and leading to oligospermia or azoospermia. Moreover, serious systemic diseases, malnutrition and a series of drugs can also affect the release of gonadotropin-releasing hormone (GnRH). For example, long-term treatment with high-dose glucocorticoid or opioids can inhibit GnRH release and induce hypogonadotropic hypogonadism (HH) and oligospermia. Similarly, antipsychotic treatment by inducing hyperprolactinemia can also induce the situation. Severe systemic diseases often lead to secondary spermatogenic failure, while certain systemic diseases (such as human immunodeficiency virus abbreviated as HIV or iron overload syndrome) may lead to primary and secondary loss of spermatogenic function. Genetic problems are also common in oligospermia, in which microdeletion of the long arm of Y chromosome (Yq) is the most common genetic cause of spermatogenesis failure. The microdeletion of Yq involves the azoospermic factor (AZF) region, which contains multiple replicated spermatogenic genes. Finally, the maturation and development of sperm are inseparable from the regulation of hypothalamus-pituitary-testis axis, and any inhibition of gonadotropin secretion will produce a downstream effect of interrupting the biosynthesis of testosterone and spermatogenesis in testis.

In fact, even after a comprehensive examination, 60% to 75% of men still cannot get a clear diagnosis to explain their oligospermia. In severe HH, the symptoms of sexual dysfunction, micropenis, small testis and azoospermia are obvious, but in some HH, the intermediate phenotype of oligospermia may appear. In chemotherapy-induced spermatogenic failure, the only characteristic may be a decrease in testicular volume. In the abuse of androgens, oligospermia may be accompanied by signs of hyperandrogenism (acne, excessive muscle development) and small testis. Therefore, the clinical evaluation of oligospermia should consider multiple factors, such as whether there is a history of sexually transmitted infections, genital infections, mumps or surgery (especially cryptorchidism or torsion), androgen deficiency, and other reproductive tract diseases, and also consider general health issues, such as systemic diseases, malignant tumors, prescription or other drug use, occupational environment, and lifestyle. In addition, it should also be considered from the patient's semen analysis, hormone assessment, genetic testing and other aspects.

Clinical treatment for patients with oligospermia includes discontinuing the use of drugs known or suspected to have adverse effects on fertility. For men with unexplained oligospermia, it is recommended to consider assisted reproductive technology. For males with unexplained oligospermia, assisted reproductive technology is recommended. In addition, vitamins and antioxidants have been widely used to improve fertility, but there are few successful data. In drug therapy, gonadotropin therapy can significantly increase the amount of spermatogenesis. For example, 80% of patients can recover spermatogenesis after 3-6 months of combined treatment with human chorionic gonadotropin (hCG) and recombinant follicle stimulating hormone (rFSH), or 77% of patients can succeed in spermatogenesis through GnRH supplementation. However, hormone supplementary therapy needs to strictly control the dosage, monitor the changes of hormones in the body on time and adjust the dosage in time. The operation is troublesome, the treatment cycle is long, and long-term injection is also easy to aggravate the pain and economic burden of patients. More importantly, long-term hormone therapy is easy to cause endocrine disorder, induce cardiovascular diseases and may be accompanied by obesity, which aggravates the physical burden of patients. In addition, selective estrogen receptor modulators (SERMs), such as clomiphene citrate, have been proven to be useful in men with oligospermia with hypogonadism. Although clomiphene has the advantage of oral administration, it is not suitable for long-term use, because researches have shown that just 12-month treatment can significantly reduce the bone mineral density of patients. Therefore, in the treatment of oligospermia, it is particularly important to discover a small molecule compound with small side effects, oral administration, fast efficacy, and low cost.

Riluzole, 2-amino-6-trifluomethoxy-benzothiazole, is the only drug approved by the U.S. Food and Drug Administration (FDA) for the treatment of amyotrophic lateral sclerosis (ALS), which can significantly extend the life of patients. In addition, riluzole also has a wide range of pharmacological effects, such as regulating glutamic acid and its transporters, neuroprotective effects, antidepressant, antiepileptic and so on. Therefore, riluzole as a drug has a good development and application prospects. At present, there is no report on the application of riluzole in the treatment of oligospermia.

SUMMARY

In order to overcome serious side effects of gonadotropin therapy in a current treatment of oligospermia, one purpose of the disclosure is to provide a small molecule compound riluzole to treat oligospermia and solve the technical problems of male oligospermia or azoospermia at present.

Specifically, an oligospermia model is established by a single intraperitoneal injection of busulfan 30 milligrams per kilogram (mg/kg) in 4-week-old male Kunming mice. After the model is successfully established, riluzole (3 mg/kg, 6 mg/kg) is injected intraperitoneally for 7 consecutive days or oral riluzole (5 mg/kg). After 10 weeks, the effect of riluzole on the treatment of oligozoospermia is evaluated by analyzing histomorphology of the testis and epididymis of mice, a sperm count, a sperm motility and a sperm morphology. Experiments have shown that intraperitoneal injection or oral administration of riluzole has a therapeutic effect on the oligospermia. Details are described in the following embodiments. Thus, the disclosure is achieved.

Therefore, in one aspect, the disclosure provides an application method of riluzole or a prodrug thereof in preparation of drugs for treating subjects with the oligospermia. It is generally believed that the oligospermia occurs when sperm count in semen is less than 20 million per milliliter.

The riluzole is a member of the benzothiazole class, named as 2-amino-6-trifluomethoxy-benzothiazole with a chemical formula $C_8H_5F_3N_2OS$, a molecular weight of the riluzole is 234.2, and a melting point of the riluzole is 116-118° C. The riluzole is a product obtained by the reaction of 4-trifluoromethoxyaniline and $NH_4CN_S$ in acetic acid, and then reacted with bromine at 5-10° C. overnight. A yield of the riluzole is about 75%, and a structural formula is expressed as follow:

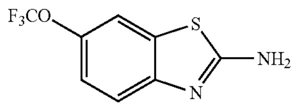 [SMILES: Nc1nc2ccc(OC(F)(F)F)cc2s1]

In an embodiment, the subject is (male) vertebrates or rodents. In a specific embodiment, the subject is mammals. In another specific embodiment, the subject is human and non-human primates, rabbits, rats, and mice, etc.

In an embodiment, the drug is suitable for oral, sublingual, nasal, local, pulmonary, percutaneous, or parenteral administration, such as rectal, subcutaneous, intravenous, urethral, intramuscular, or nasal administration. In a specific embodiment, the drug is suitable for oral or intraperitoneal injection.

In an embodiment, the drug is in a form of tablets, coated tablets, dragee, pills, cachet, hard or soft gelatin capsules, solutions, emulsions, suspensions, suppositories, ointments, aerosols, or injections.

The riluzole or the prodrug thereof can be processed with pharmaceutically inert, inorganic or organic carriers for the preparation of pharmaceutical preparations. For example, lactose, corn starch or derivatives of lactose and corn starch, talc, stearic acid or stearic acid salts can be used as a carrier for tablets, coated tablets, dragee and hard gelatin capsules. The carrier suitable for soft gelatin capsules are such as vegetable oil, wax, fat, semi-solid and liquid polyols. However, depending on the nature of the active substance, the carrier is usually not required in a case of soft gelatin capsules. The carrier suitable for the preparation of solutions and syrups is water, polyols, glycerol, vegetable oil, etc. The carrier suitable for suppositories is natural or hardened oils, waxes, fats and semi-liquid or liquid polyols.

In addition, pharmaceutical preparations can contain pharmaceutical adjuvant substances, such as preservatives, solubilizers, stabilizers, wetting agents, emulsifiers, sweeteners, colorants, flavor enhancers, salts used to change osmotic pressure, buffer agents, masking agents or antioxidants, which can also contain other substances of therapeutic value.

The dose can vary over a wide range, and of course, it must be adjusted according to individual needs in each specific case. In a case of oral administration, the dose for adults can change from about 0.01 mg/kg body weight per day to about 1000 mg/kg body weight per day of the riluzole or the prodrug thereof. The daily dose can be administered at a single dose or at a separate dose, moreover, the upper limit can be exceeded when needed.

In an embodiment, the oligospermia is caused by one or more of the following: testicular injury, cancer therapy (e.g., chemotherapy, such as busulfan, or radiotherapy), severe systemic diseases, malnutrition, drug abuse, anti-psychotherapy, or genetic issues.

In an embodiment, the prodrug refers to a compound that is lysed by an enzymatic or general biophysical release method to release the riluzole into plasma.

The prodrug of riluzole is described as follows: the U.S. Pat. No. 9,725,427 issued on Aug. 8, 2017, U.S. patent application Ser. No. 14/410,647 submitted on Dec. 23, 2014, U.S. patent application Ser. No. 15/549,154 submitted on Aug. 5, 2017, patent cooperation treaty (PCT) application serial number PCT/US2016/019773 submitted on Feb. 26, 2016, and PCT application serial number PCT/US2016/019787 submitted on Feb. 26, 2016.

In an embodiment, the prodrug of riluzole is a compound of the following formula disclosed in Chinese patent of CN112469408A and CN107567438B:

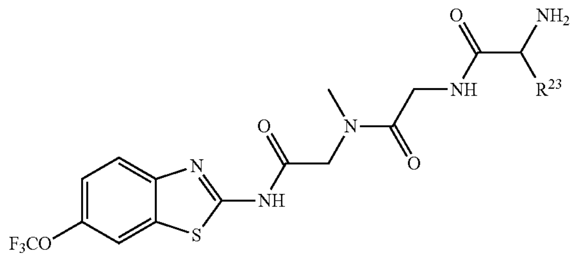

or a pharmaceutically acceptable salt of the compound, where $R^{23}$ is selected from the group consisting of H, $CH_3$, $CH_2CH_3$, $CH_2CH_2CH_3$, $CH_2CCH$, $CH(CH_3)_2$, $CH_2CH(CH_3)_2$, $CH(CH_3)CH_2CH_3$, $CH_2OH$, $CH_2OCH_2Ph$, $CH_2CH_2OCH_2Ph$, $CH(OH)CH_3$, $CH_2Ph$, $CH_2$ (cyclohexyl), $CH_2$(4-OH-Ph), $(CH_2)_4NH_2$, $(CH_2)_3NHC(NH_2)NH$, $CH_2$(3-indole), $CH_2$(5-imidazole), $CH_2CO_2H$, $CH_2CH_2CO_2H$, $CH_2CONH_2$and $CH_2CH_2CONH_2$, and the Ph represents phenyl.

Chinese patent of CN112469408A and CN107567438B proved that the prodrug of riluzole can release the riluzole into plasma in vivo to exert the therapeutic activity of the riluzole.

In an embodiment, the formula of the prodrug that is a compound is expressed as follows:

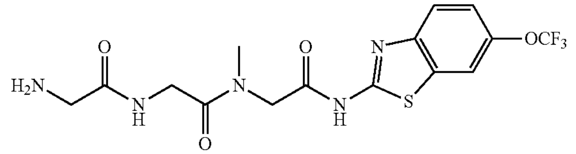 [SMILES: CN(CC(=O)Nc1nc2ccc(OC(F)(F)F)cc2s1)C(=O)CNC(=O)CN]

In an embodiment, the riluzole or the prodrug thereof is used in combination with another drug or therapy for treating the oligospermia.

In an embodiment, the another drug and the therapy is selected from the group consisting of vitamins, antioxidant, human chorionic gonadotropin (hCG), recombinant human follicle-stimulating hormone (rFSH), gonadotropin-releasing hormone (GnRH), selective estrogen receptor modulators, and a combination of them.

Compared with the treatment of oligospermia in the related art, the disclosure has the following advantages.

(1) The treatment of oligospermia has the advantages of less side effects, rapid onset, low cost and oral administration. The riluzole can be rapidly absorbed after oral administration, an absolute bioavailability of the riluzole is about 60% and the riluzole reaches the peak of blood concentration within 60-90 minutes after administration. In addition, the riluzole shows a good tissue distribution, with a volume of distribution (Vd) of about 3.4 liters per kilogram (L/kg).

(2) Compared with traditional Chinese medicines with unclear targets and unknown active ingredients, the riluzole, as a small molecule compound, can enter the blood-testis barrier (BTB), thus restoring the integrity of the blood-testis barrier, protecting germ cells from toxic substances, and ensuring the orderly progress of spermatogenesis.

(3) Compared with hormone drugs that are easy to cause endocrine disorders and induce cardiovascular diseases, the riluzole has no obvious side effects, and a use of the riluzole in the treatment of oligospermia cannot aggravate the physical burden of patients.

DETAILED DESCRIPTION OF EMBODIMENTS

Figure 1:
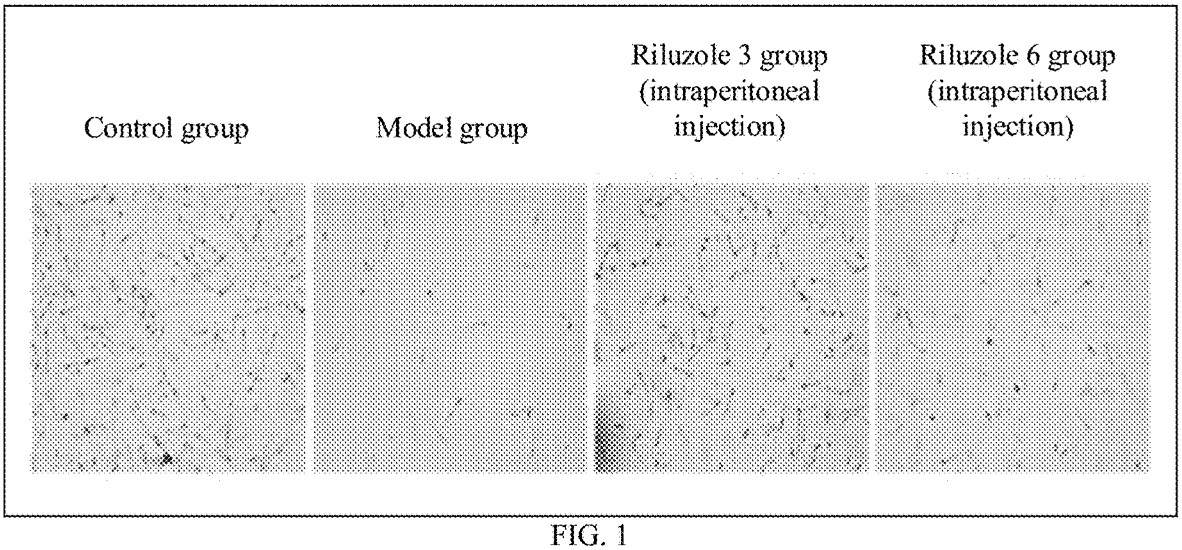
FIG. 1 is a sperm capture diagram of a tail of epididymis of busulfan-modeled mice after intraperitoneal administration of riluzole (3 milligrams per kilogram abbreviated as mg/kg, 6 mg/kg) for seven consecutive days.
Figure 2A:
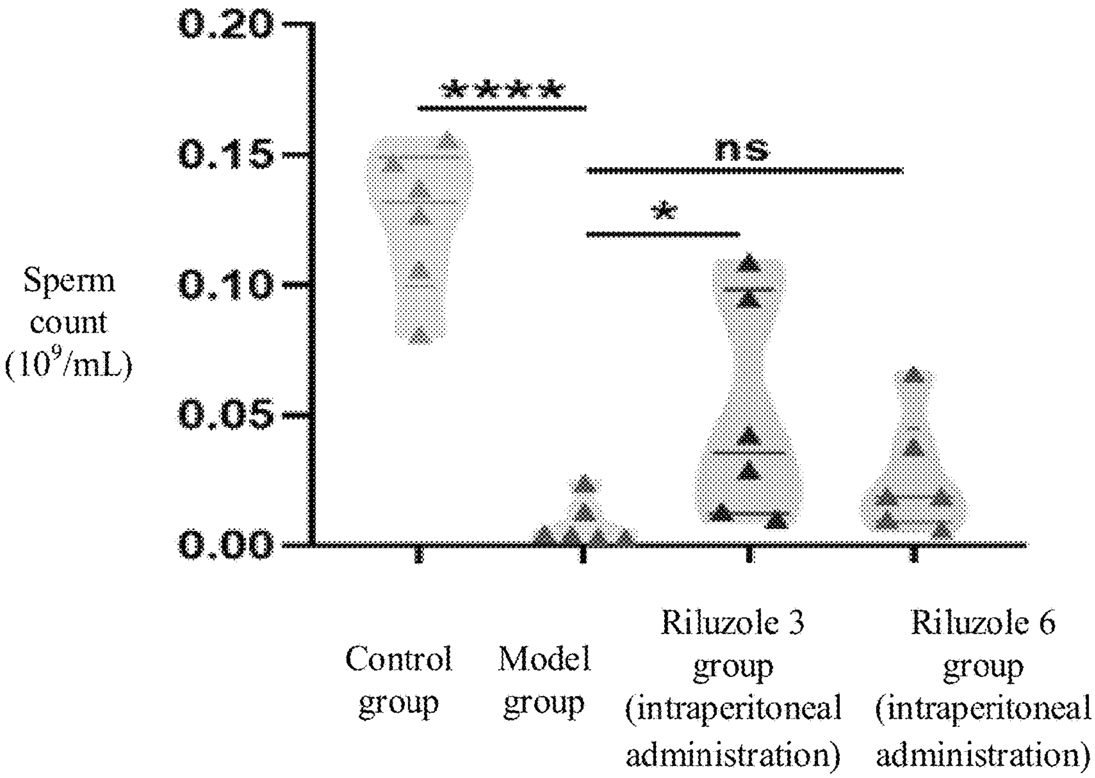
FIGS. 2A-2D are diagrams showing sperm count, sperm survival rate, sperm motility rate and sperm abnormality rate in the tail of epididymis of the busulfan-modeled mice after intraperitoneal administration of riluzole (3 mg/kg, 6 mg/kg) for seven consecutive days analyzed by a computer-aided sperm analyzer (CASA).
Figure 2B:
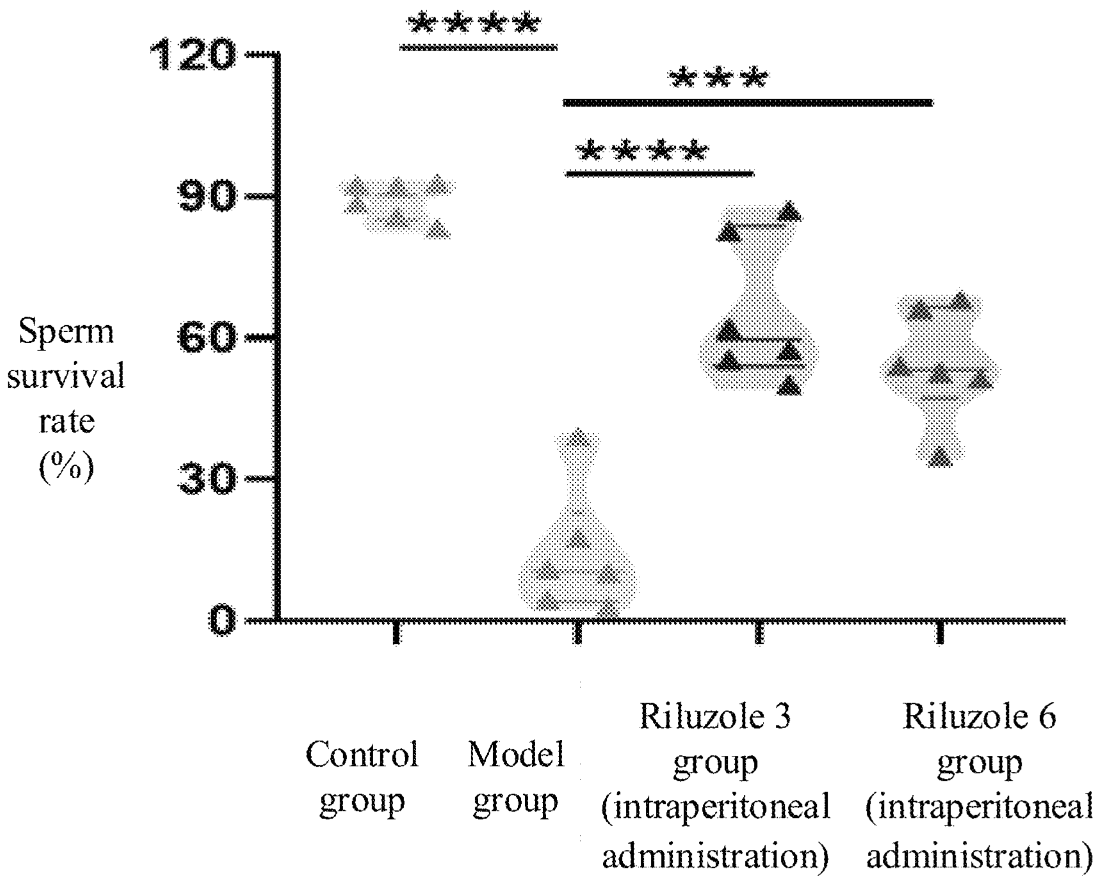
Figure 2C:
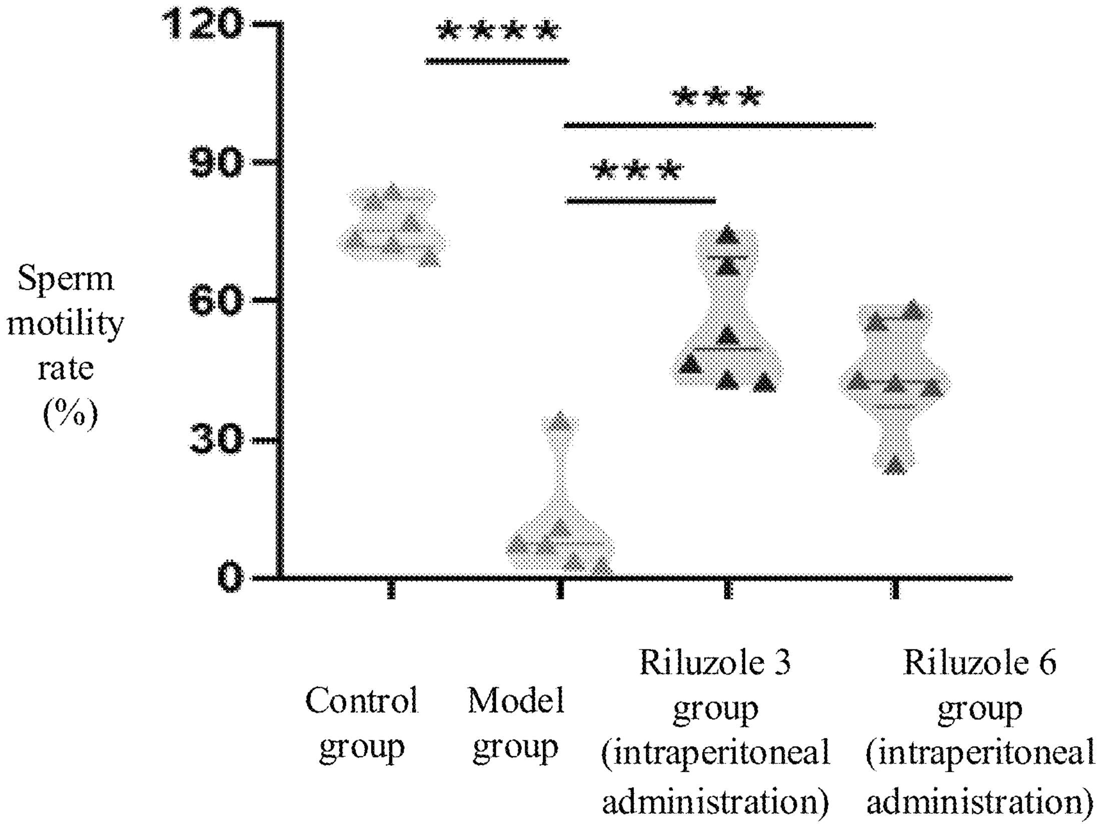
Figure 2D:
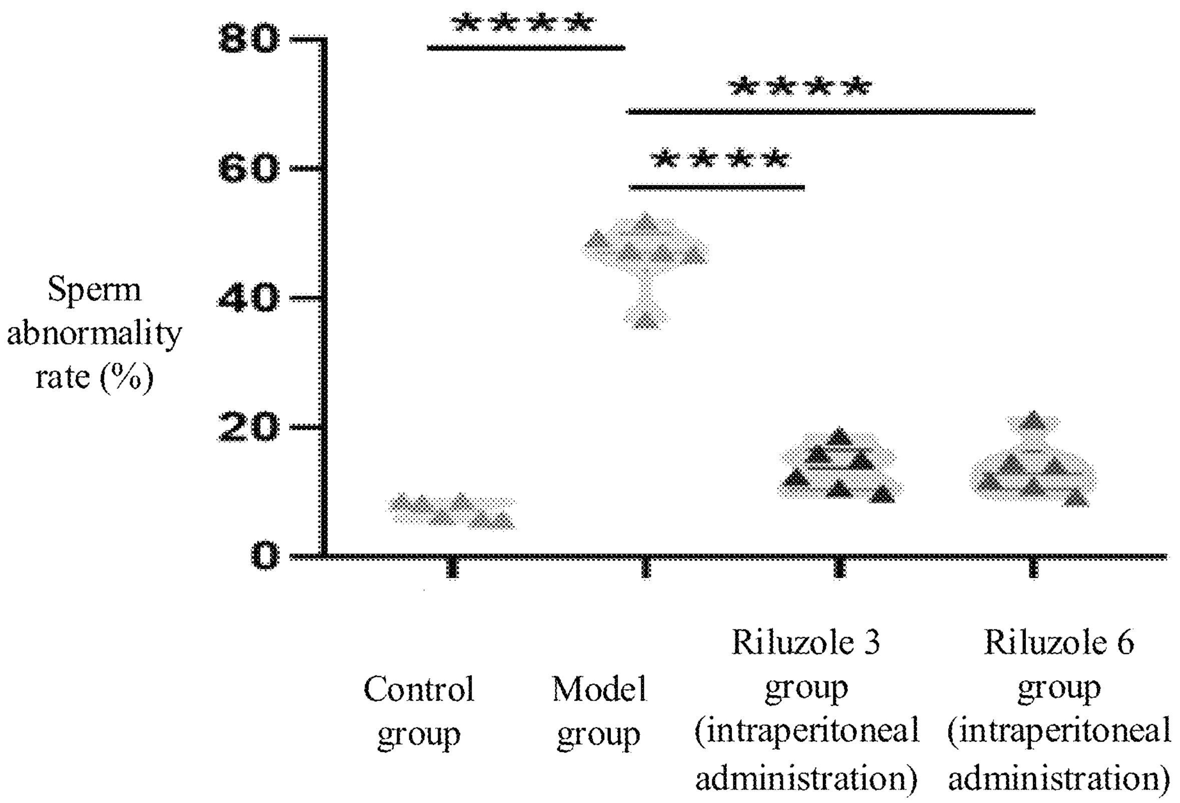
Figure 3A:
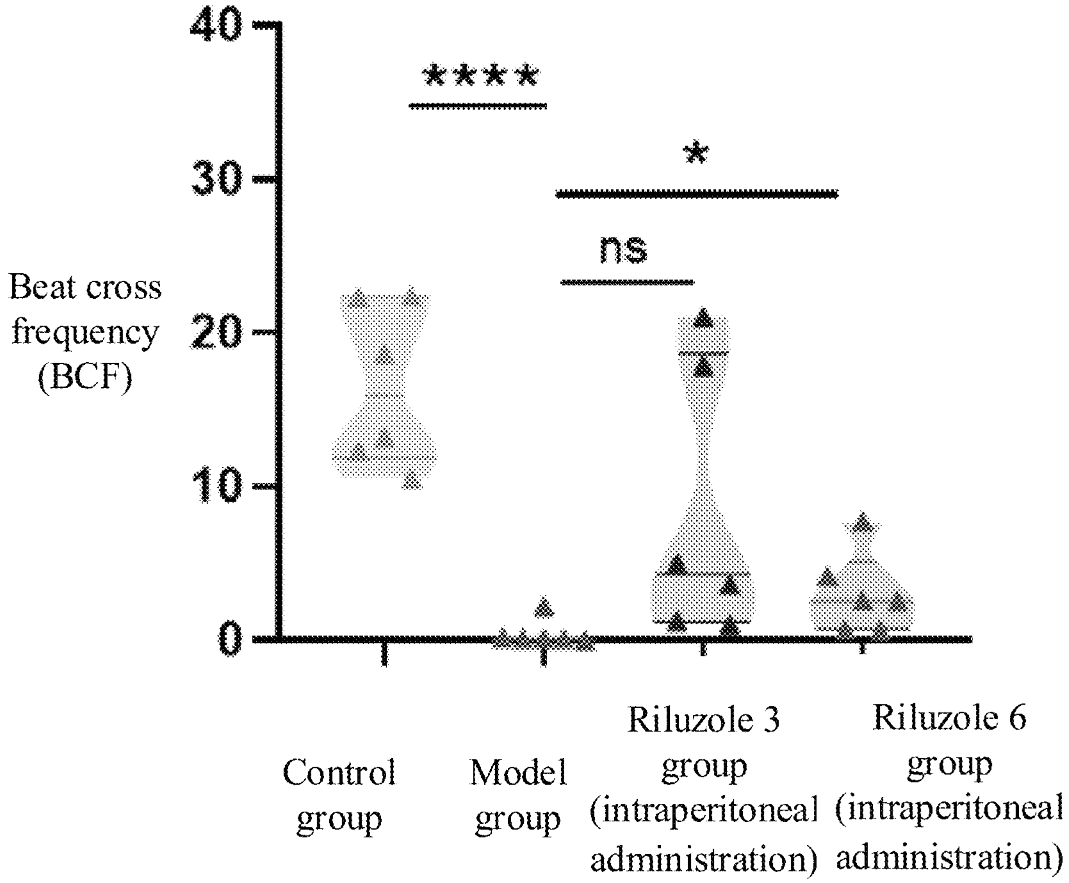
FIGS. 3A-3D are diagrams showing beat cross frequency (BCF), straight line velocity (VSL), amplitude of lateral head displacement (ALH) and straightness (STR) of the sperm in the tail of epididymis of the busulfan-modeled mice after intraperitoneal administration of riluzole (3 mg/kg, 6 mg/kg) for seven consecutive days analyzed by the CASA.
Figure 3B:
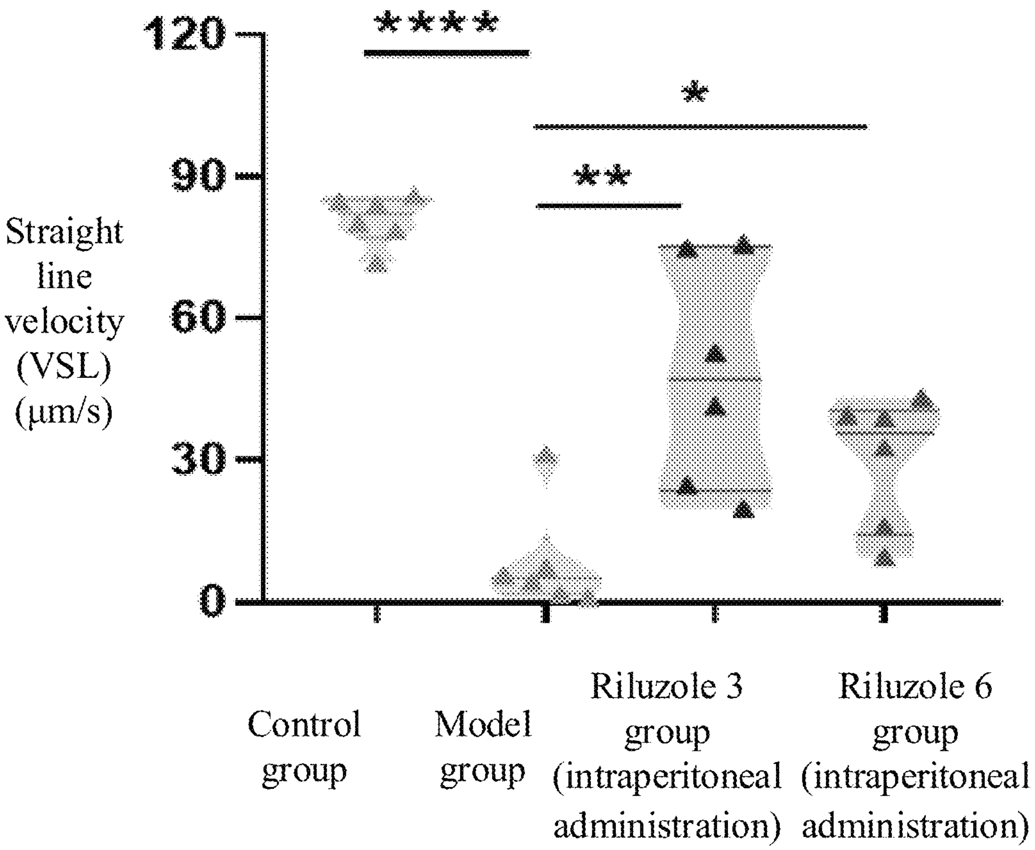
Figure 3C:
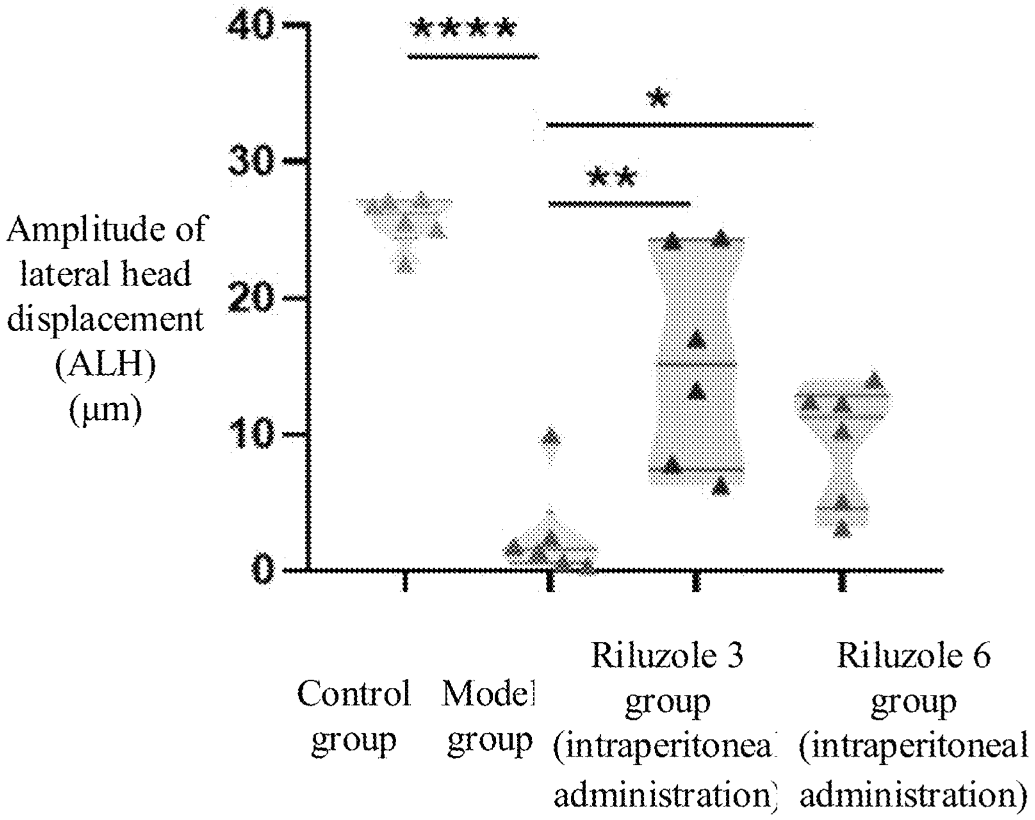
Figure 3D:
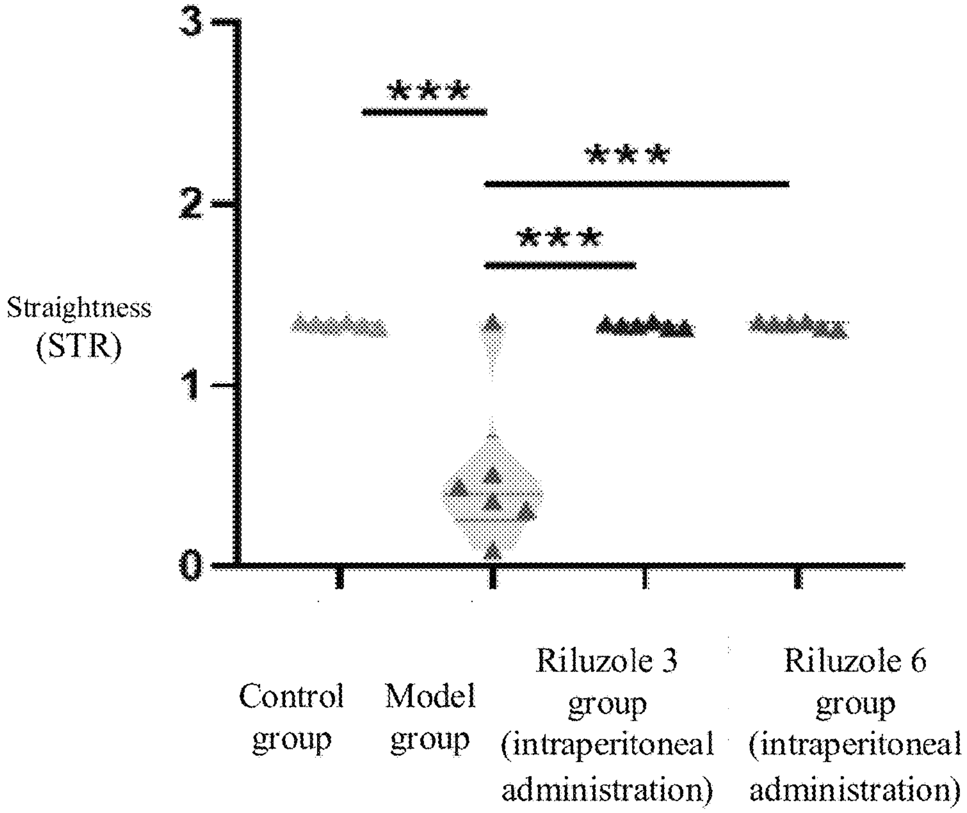

Unless otherwise indicated, terms used herein have general technical meanings understood by those skilled in the art.

Technical solutions of the disclosure are explained in combination with embodiments. Those skilled in the art can understand that the following embodiments are only used to illustrate the disclosure and should not be considered as limiting the scope of the disclosure. If the specific technologies or conditions are not specified in the embodiments, the technologies or conditions described in the literatures in this field or the instruction of product shall be followed. The reagents or instruments used without specifying the manufacturer are all conventional products that can be obtained through commercial purchase.

Reagents

1. Busulfan (MedChemExpress LLC); 2. Riluzole (Selleck Chemicals LLC); 3. optimal cutting temperature (OCT) compound (Sakura Finetek USA, Inc.); 4. paraformaldehyde (Sigma-Aldrich®); 5. 4',6-diamidino-2-phenylindole (DAPI) staining solution (Boster Biological Technology.); 6. anti-synaptonemal complex protein 3 (SYCP3) antibodies (Abcam plc.); 7. Alexa Fluor® 488 AffiniPure Goat Anti-Rabbit IgG (Abcam plc.); 8. Sulfo-NHS-LC-Biotin (Thermo Fisher Scientific.); 9. Alexa Fluor™ 568 streptavidin conjugate (Thermo Fisher Scientific.)

Embodiment 1 Experimental Animal Modeling and Administration Regimen (1) Raising of Experimental Animal Fifty 4-week-old Kunming male mice are purchased from Guangdong medical laboratory animal center (GDMLAC) and raised in 10 cages (5 mice per cage). During the feeding or experimental period, a room temperature is controlled at 25±1° C., the light-dark cycle is 12 hours of light, 12 hours of darkness, humidity 50-60%, and the mice are free to eat. Follow-up experiments are carried out three days after the mice adapted to the environment.

(2) Grouping the Experimental Animal

A grouping situation is as follows:

1. control group: physiological saline (10 mice);
2. model group: busulfan (30 mg/kg) +dimethyl sulfoxide (DMSO) (10 mice);
3. riluzole 3 (intraperitoneal injection) group: busulfan (30 mg/kg)+riluzole (3 mg/kg, intraperitoneal injection) (10 mice);
4. riluzole 6 (intraperitoneal injection) group: busulfan (30 mg/kg)+riluzole (6 mg/kg, intraperitoneal injection) (10 mice); and riluzole 5 (oral administration) group: busulfan (30 mg/kg)+riluzole (5 mg/kg, intraperitoneal injection) (10mice).

(3) Experimental Animal Modeling

The Kunming mice are injected intraperitoneally with busulfan (30 mg/kg). An average weight of the mice is 27 grams (g). Each mouse is injected with 0.8 mg busulfan. A total of 40 mice are modeled.

Preparation of a busulfan solution is as follows:

1. weighing and dissolving 40 mg busulfan powder in 2.5 mL DMSO;
2. adding 2.5 milliliters (mL) of phosphate buffered saline (PBS) preheated to 50° C. in advance to further dilute and keep warm in a hot water bath to prevent drug precipitation; and
3. injecting 100 microliters (uL) busulfan solution in each mouse intraperitoneally, and injecting equivalent amount of physiological saline in the control group.

(4) Experimental Animal Administration

After one week of modeling the mice, the average weight of the experimental mice is grams (g). The administration groups are intraperitoneally injected or orally administered with riluzole for seven consecutive days. The control group and the model group are injected with the equivalent amount of physiological saline.

(5) Experimental Animal Sacrificing and Sampling Under Anesthesia

After the mice are anesthetized and sacrificed, the left epididymal tail is immediately removed for semen analysis. The left testis is stored at −80° C., and the parameters such as protein and messenger ribonucleic acid (mRNA) expression are detected. The right testis and right epididymis are fixed with 4% paraformaldehyde for further histological analysis.

Embodiment 2 Analyzing Semen of Experimental Animals

Figure 8:
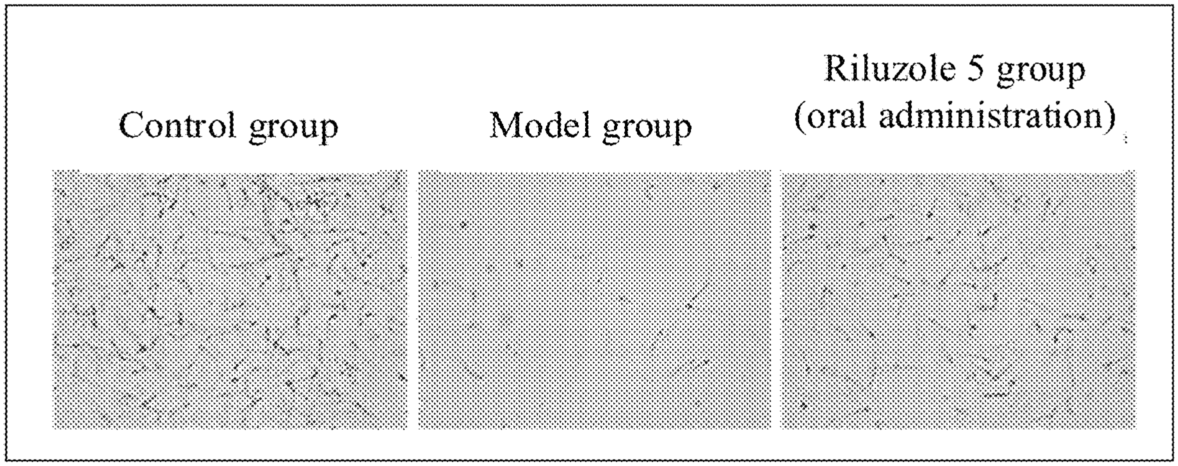
FIG. 8 is a sperm capture diagram of a tail of epididymis of busulfan-modeled mice after oral administration of riluzole (5 mg/kg) for seven consecutive days.
Figure 9A:
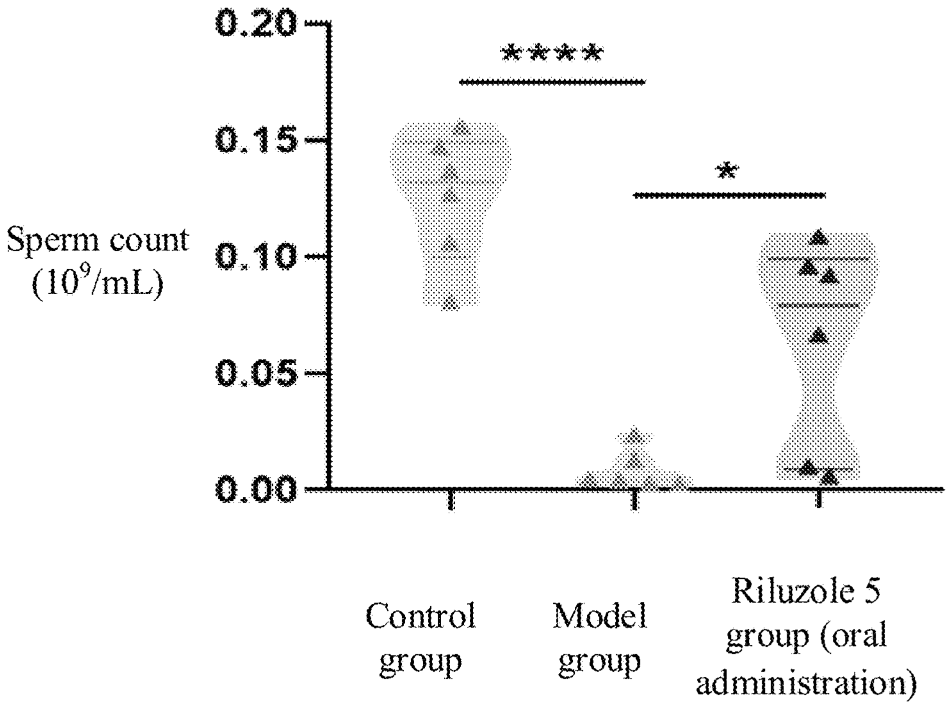
FIGS. 9A-9D are diagrams showing sperm count, sperm survival rate, sperm motility and sperm abnormality rate in the tail of epididymis of the busulfan-modeled mice after oral administration of riluzole (5 mg/kg) for seven consecutive days analyzed by the CASA.
Figure 9B:
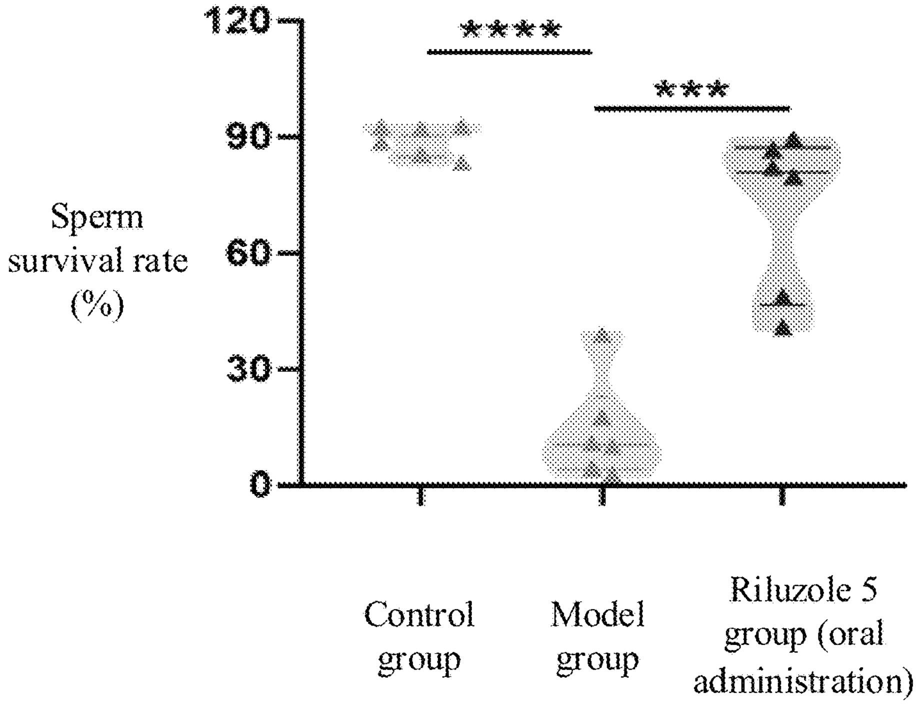
Figure 9C:
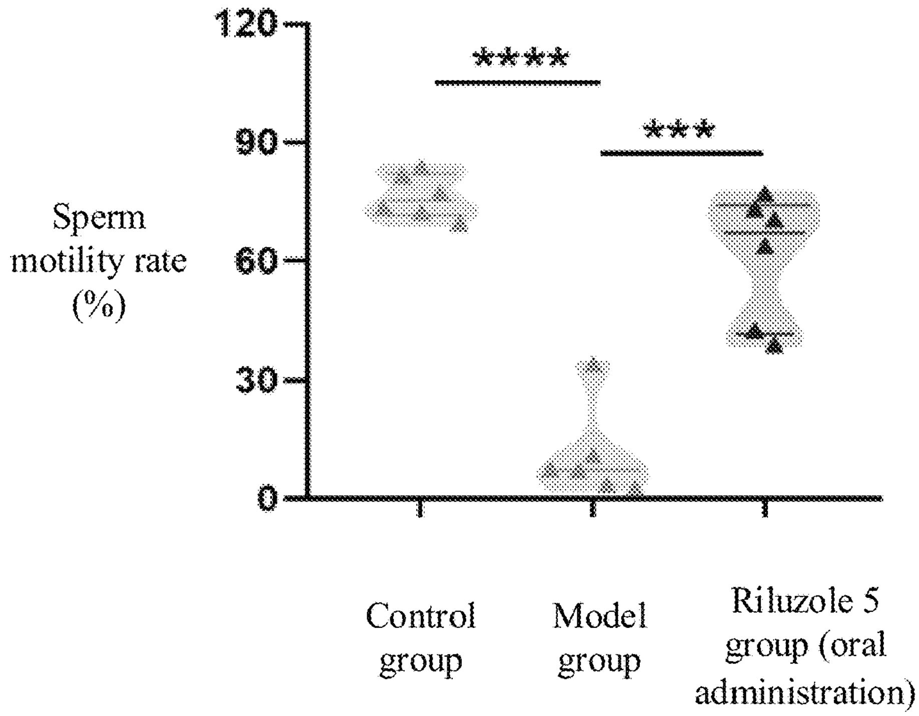
Figure 9D:
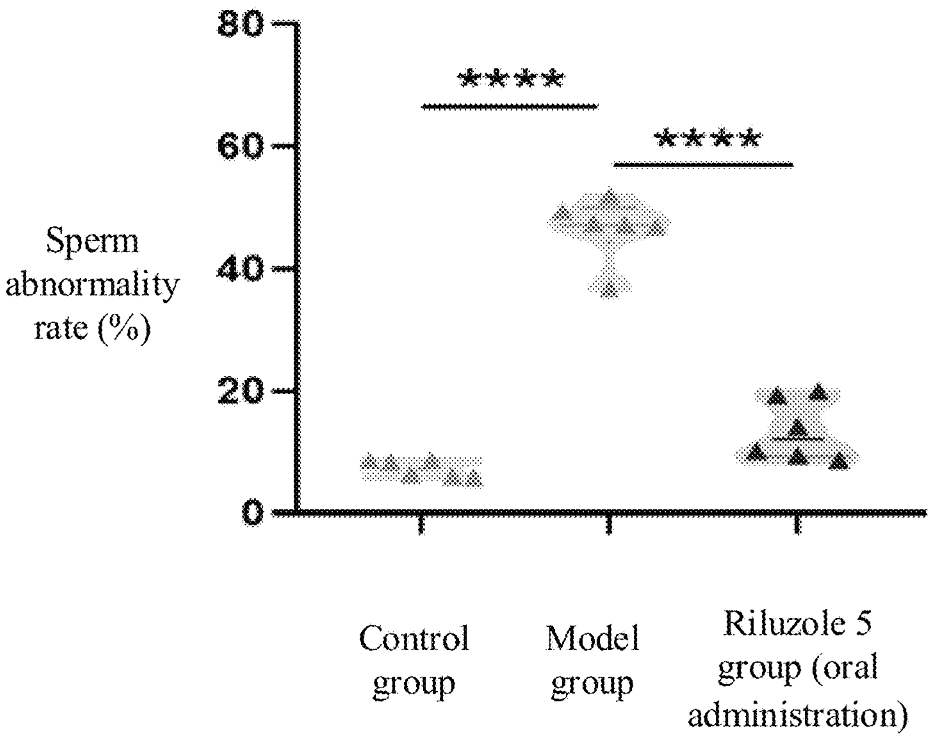
Figure 10A:
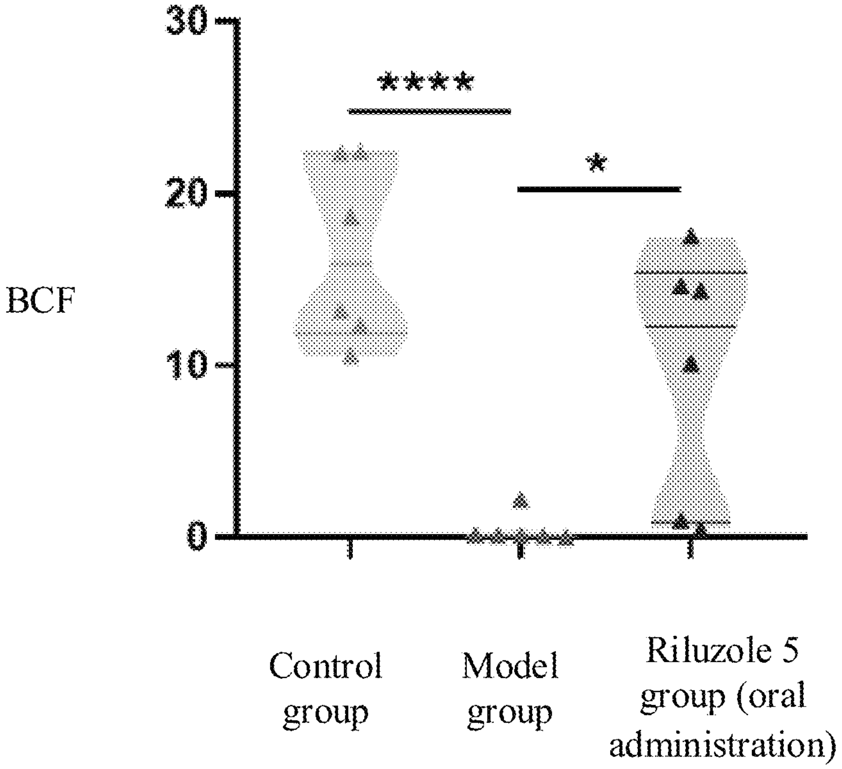
FIGS. 10A-10D are diagrams showing BCF, VSL, ALH of the sperm and STR in the tail of epididymis of the busulfan-modeled mice after oral administration of riluzole (5 mg/kg) for seven consecutive days analyzed by the CASA.
Figure 10B:
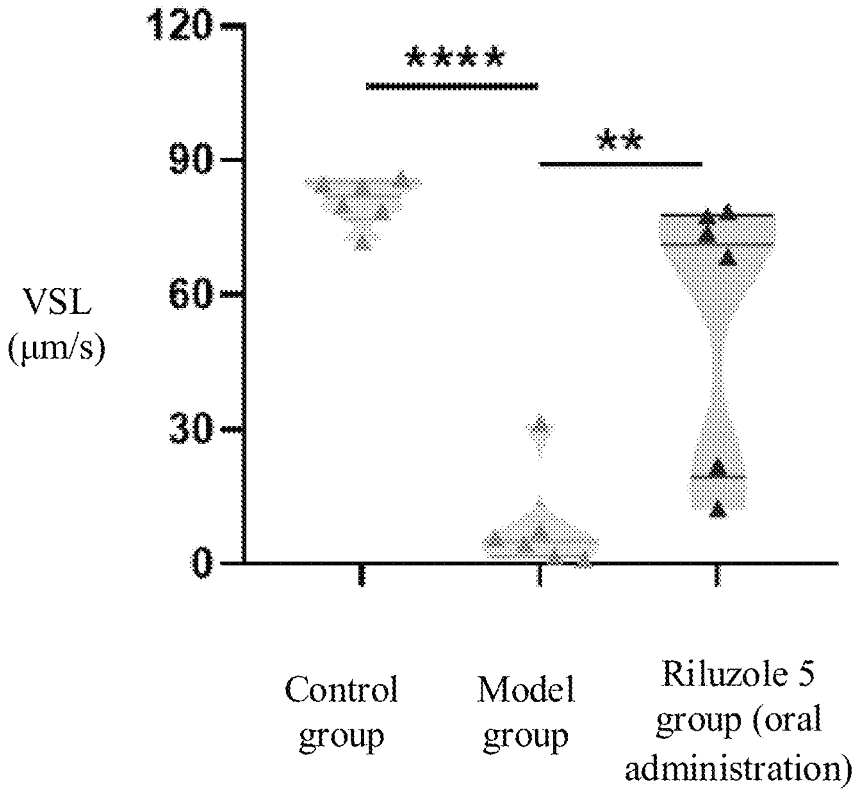
Figure 10C:
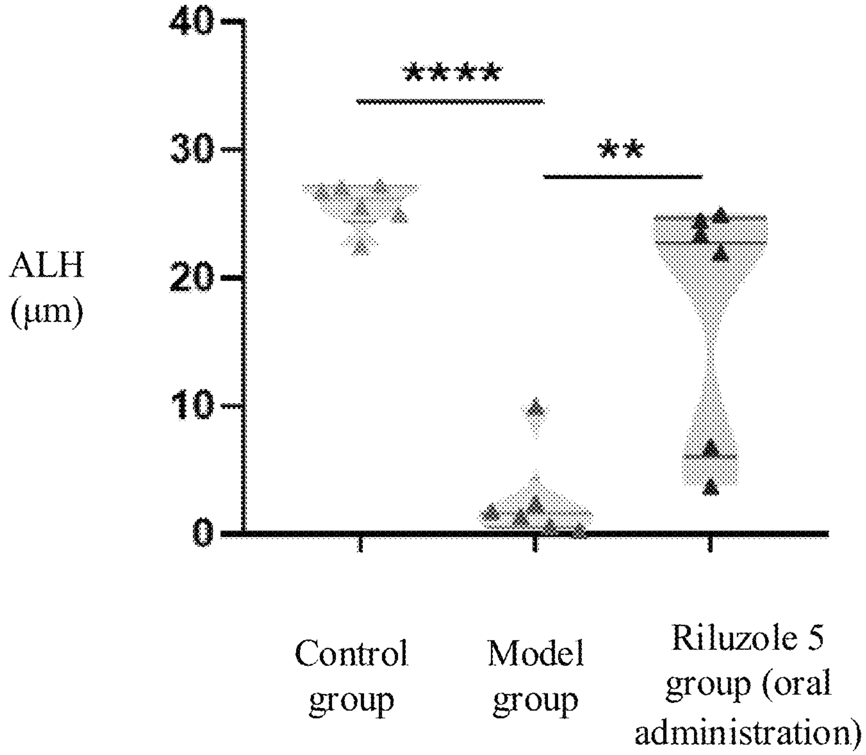
Figure 10D:
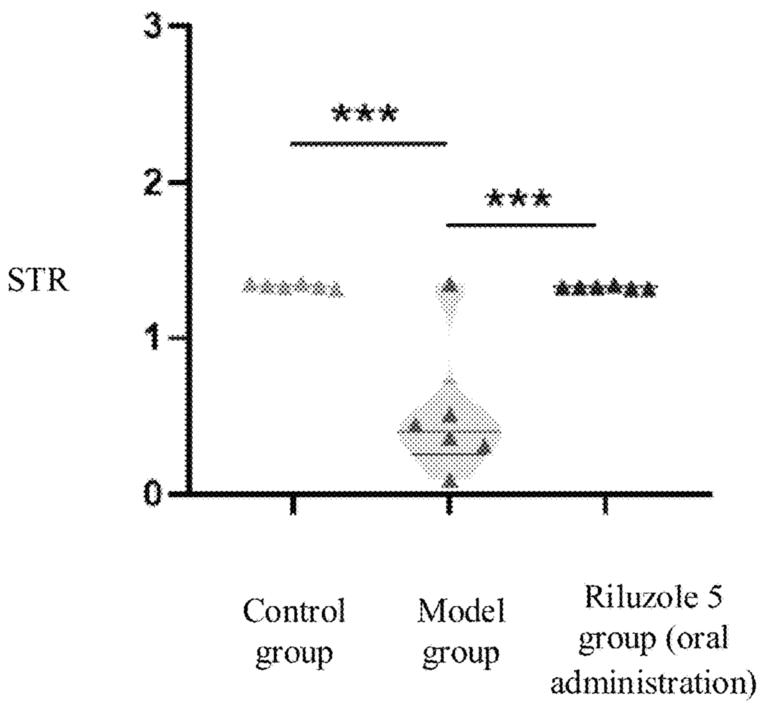

The left epididymis tail of the mouse is cut off and placed into 1 mL of PBS preheated to 37° C. In the situation, the tissue is manually cut and incubated in a 37° C. water bath for 10 minutes to fully release the sperm. The sperm suspension is mixed well, then 10 μL of the sperm suspension is aspirated and added into to a mouse-specific sperm counting plate with a depth of 60 micrometers (μm), 30 visual fields are at least captured per mouse, and the parameters such as sperm concentration, sperm survival rate, sperm motility rate, and sperm abnormality rate are comprehensively evaluated by using a computer-aided sperm analysis (CASA) (ML-810JZ, Nanning Songjing Tianlun Bio-technology Co., Ltd.). The semen analysis of the CASA system shows that compared with the model group, intraperitoneal injection or oral administration of the riluzole increases the number of sperm in the model mice (FIG. 1 and FIG. 8), promotes sperm regeneration, increases the sperm survival rate and the sperm motility rate, and significantly reduces the sperm abnormality rate (FIGS. 2A-2D and FIGS. 9A-9D), while increasing beat cross frequency (BCF) of the sperm, straight line velocity (VSL) of the sperm, amplitude of lateral head displacement (ALH) of the sperm and straightness (STR) of the sperm (FIGS. 3A-3D and FIGS. 10A-10D).

Embodiment 3 Hematoxylin and Eosin (HE) Staining of Paraffin Sections of Testis and Epididymis (1) Dewaxing and rehydration: after baking sections at 60° C. for 1 hour, the baked sections are soaked in xylene for 15 minutes 2 times, anhydrous ethanol for 5 minutes, 95% ethanol for 5 minutes, 80% ethanol for 5 minutes, 70% ethanol for 5 minutes, PBS for 5 minutes 3 times.

(2) Staining with hematoxylin: the soaked sections are taken out and dried, a hematoxylin staining solution is added to cover the tissue and stained for 3 minutes. Then, the stained sections are gently rinsed with tap water for 2-3 times, immersed in ultrapure water, and the staining is observed under the microscope, then a blue-purple nucleus can be observed.

(3) Differentiation: a differentiation solution is dropped at the sections, after 5-6 seconds (s), when observing that the color has faded, the section can be rinsed with the ultrapure water.

(4) Bluing: hematoxylin bluing solution is dropped at the section, after 5-6 seconds, when observing the color blue, the sections can be rinsed with the ultrapure water.

(5) Staining with eosin: the water stains on the sections are dried, the eosin staining solution is added to cover the tissue for 5 minutes, the staining solution is directly removed, and the stained sections with eosin are soaked in anhydrous ethanol for 10 minutes twice to remove the floating color. Under the microscope, the cytoplasm is bright and light red, and the nucleus is blue-purple.

(6) Sealing: the sections are cleared using xylene for 5 minutes and then neutral resin is applied, followed by a glass coverslip.

Figure 4:
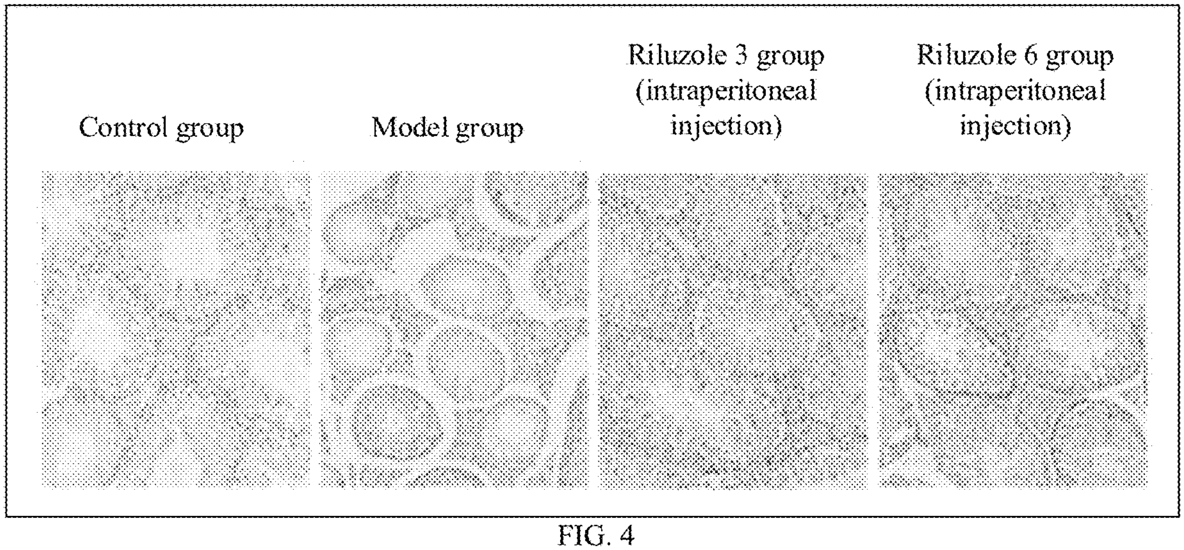
FIG. 4 is a diagram showing morphological changes of testes of the busulfan-modeled mice after intraperitoneal administration of riluzole (3 mg/kg, 6 mg/kg) for seven consecutive days detected by hematoxylin and eosin (HE) staining.
Figure 5:
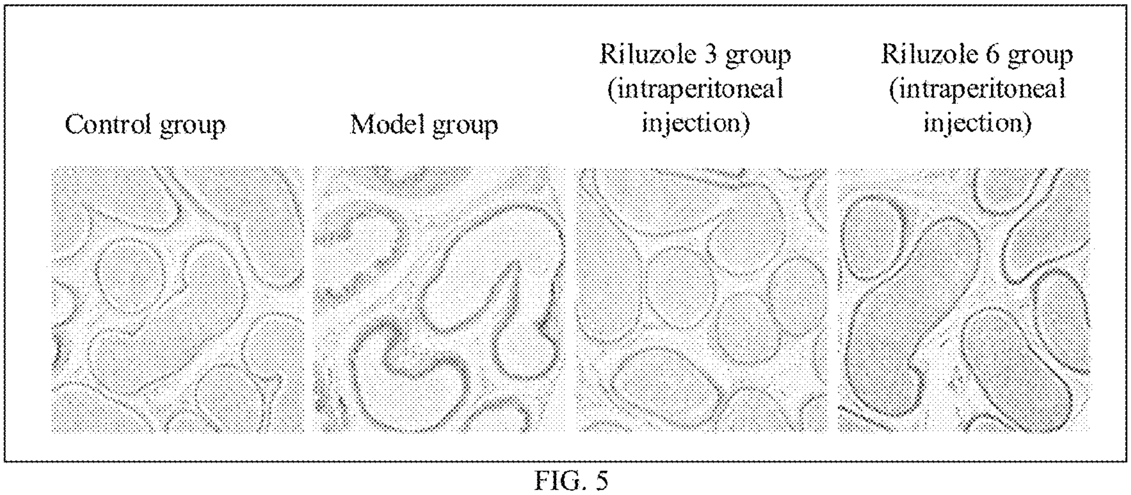
FIG. 5 is a diagram showing morphological changes of the epididymis of the busulfan-modeled mice after intraperitoneal administration of riluzole (3 mg/kg, 6 mg/kg) for seven consecutive days detected by HE staining.
Figure 11:
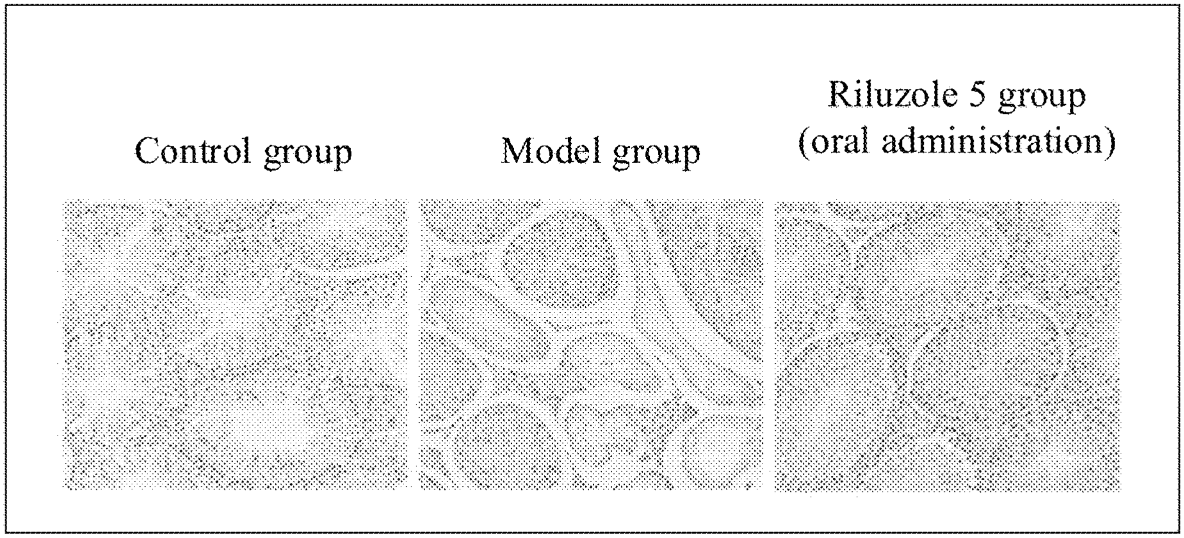
FIG. 11 is a diagram showing morphological changes of testes of the busulfan-modeled mice after oral administration of riluzole (5 mg/kg) for seven consecutive days detected by HE staining.
Figure 12:
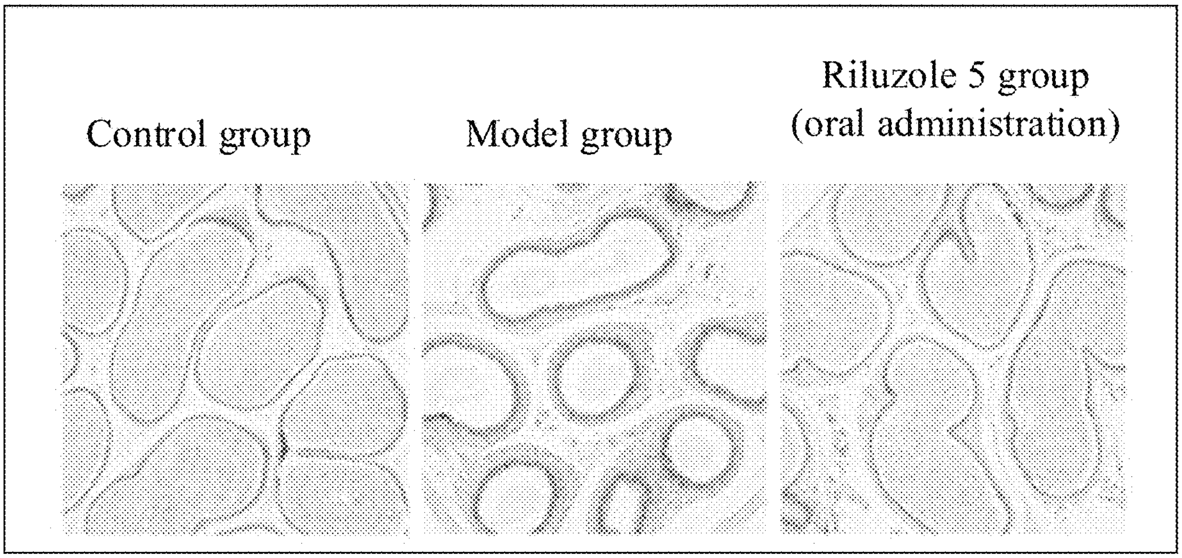
FIG. 12 is a diagram showing morphological changes of epididymis of the busulfan-modeled mice after oral administration of riluzole (5 mg/kg) for seven consecutive days detected by HE staining.

(7) Observation under microscope: the pathomorphological changes of the testes and epididymis are observed under the microscope. The HE staining of testes in the model group shows that compared with the control group, busulfan severely damages the structure of seminiferous tubules, makes the tubule wall thinner, the tubule diameter shorter, the germ cell in the basement membrane of the tubule are disappeared, the spacing between the tubules is increased, and the testes are significantly atrophied. The HE staining in the administration group shows that after intraperitoneal injection or oral administration of the riluzole, the wall of seminiferous tubules in the testis is thickened, the diameter of the tubules is increased, the germ cells in the basement membrane of the tubules are increased significantly, and the spacing between the tubules is restored to normal, which promotes the recovery of the injured testes (FIGS. 4 and 11). The HE staining of epididymis shows that there are no sperm in the seminiferous tubules of the model group, while the administration group shows some sperm regeneration in the seminiferous tubules (FIGS. 5 and 12).

Embodiment 4 Immunofluorescence Detection of Frozen Sections of Testes (1) Tissue embedding and slicing: the testicular tissue is taken and placed in an embedding box, filled with the OCT compound, embedded at −80° C. for more than 30 minutes, and then sliced by using a frozen section cutter.

(2) Permeating: the frozen sections are equilibrated with room temperature for 30 minutes, then washed with PBS for 5 minutes 3 times to remove the OCT compound; the water staining of the sections is shaken off, and an immunohistochemistry pen is used to draw a circle around the tissues, 1% Trinton-X100 solution is dropped within the histochemistry circle, and then washed with PBS for 5 minutes 3 times after 24 minutes of penetration.

(3) Blocking: the water staining of the sections is shaken off, the immunofluorescence blocking solution is added dropwise into the immunohistochemistry circle, and blocked at room temperature for 1 hour.

(4) Primary antibody incubation: the blocking solution is removed without washing, and the SYCP3 antibody (ab97672, Abcam) diluted at a ratio of 1:50 is added and incubated at 4° C. overnight. After 16 hours, the primary antibody is recovered and washed with PBS for 5 minutes 3 times.

(5) Secondary antibody incubation: the secondary antibodies (Goat anti-mouse IgG H&L, ab150113, Abcam) diluted at a ratio of 1:200 are added and incubated at room temperature for 1 hour. The secondary antibodies are discarded after 1 hour and washed with the PBS for 5 minutes 3 times.

(6) Staining nuclear: the water staining of the sections is shaken off and the DAPI staining solution is added for staining for 10 minutes, and then the staining solution is discarded and washed with the PBS for 5 minutes 3 times.

(7) Sealing: the water staining of the sections is shaken off and an anti-fluorescence sealing agent is added, a glass coverslip is covered, and photos are taken under a fluorescence microscope.

Figure 6:
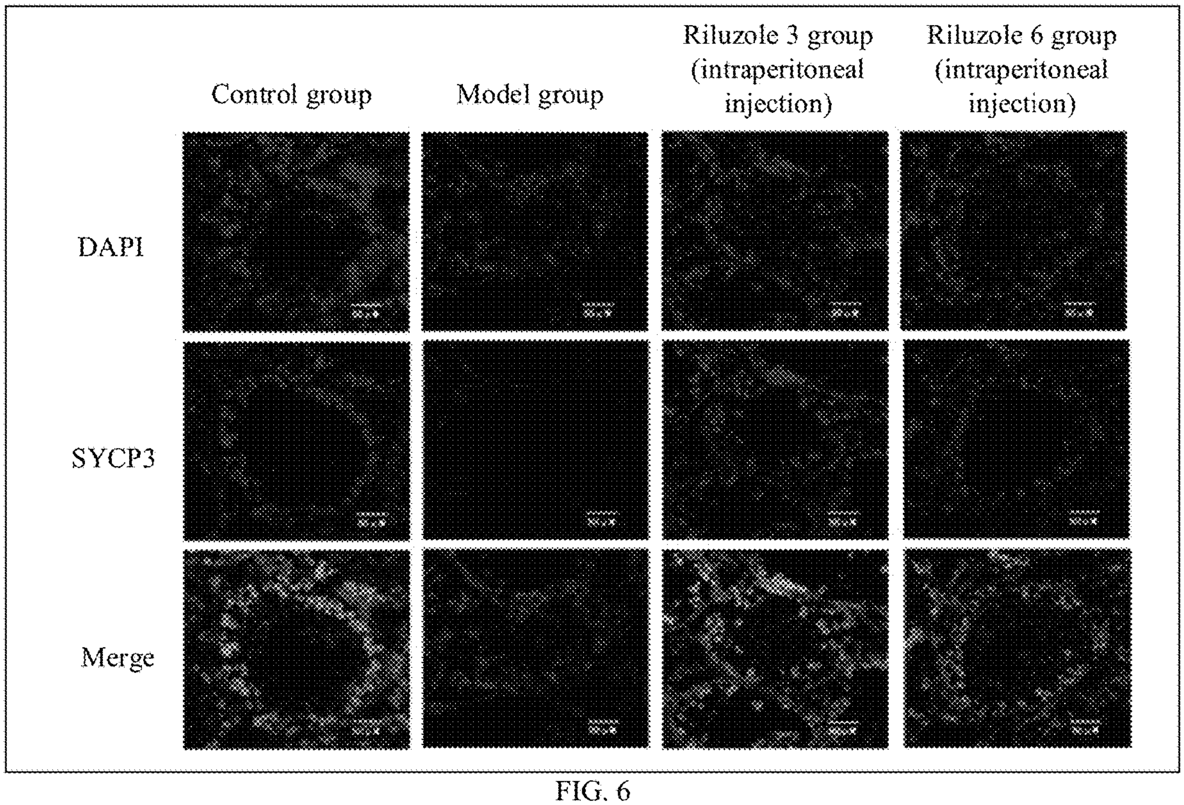
FIG. 6 is a diagram showing an expression of synaptonemal complex protein 3 (SYCP3) in the testes of the busulfan-modeled mice after intraperitoneal administration of riluzole (3 mg/kg, 6 mg/kg) for seven consecutive days detected by immunofluorescence staining.

In order to determine whether riluzole administration can promote the differentiation of spermatogonium in oligospermia model mice, the expression of spermatogonium differentiation marker protein (SYCP3) is detected by immunofluorescence. The results show that riluzole promotes the expression of SYCP3 in the testes of model mice, indicating that riluzole promotes the differentiation of spermatogonium, that is, promotes the development of sperm (FIG. 6).

Embodiment 5 Detection of Blood-Testis Barrier (BTB) Function in Mice (1) Two mice in each group are taken and tested for BTB function. The mice are anesthetized, the testes of the mice are exposed, and 30 μL Sulfo-NHS-LC-Biotin (10 mg/mL dissolved in PBS) is injected into one side of the testis.

(2) After diffusing biotin for 30-60 minutes, the mice are sacrificed, the testes are removed and embedded in a frozen section cutter, and stored at −80° C.

(3) The frozen sections of testicular tissue are prepared: the section cutter is pre-cooled to −20° C., setting a thickness of the sections is set to 6 and the sections are adhered to the labeled slides.

(4) The sections are fixed with 4% paraformaldehyde for 10 minutes, and washed the sections with PBS for 5 minutes 3 times.

(5) The sections are blocked with 5% bovine serum albumin (BSA) for 1 hour.

(6) Diluting Alexa Fluor 568 labeled streptavidin (2 mg/ml) with 1% BSA in a 1:500 ratio (starting from this step in a dark environment), incubating the sections at room temperature for 1 hour and washing with PBS for 5 minutes×3 times.

(7) Staining with DAPI for 10 minutes, washing with PBS for 5 minutes×3 times.

(8) Sealing: spin-drying the water stains, adding anti fluorescence sealing agent, covering with a cover glass, and taking photos under a fluorescence microscope.

Figure 7:
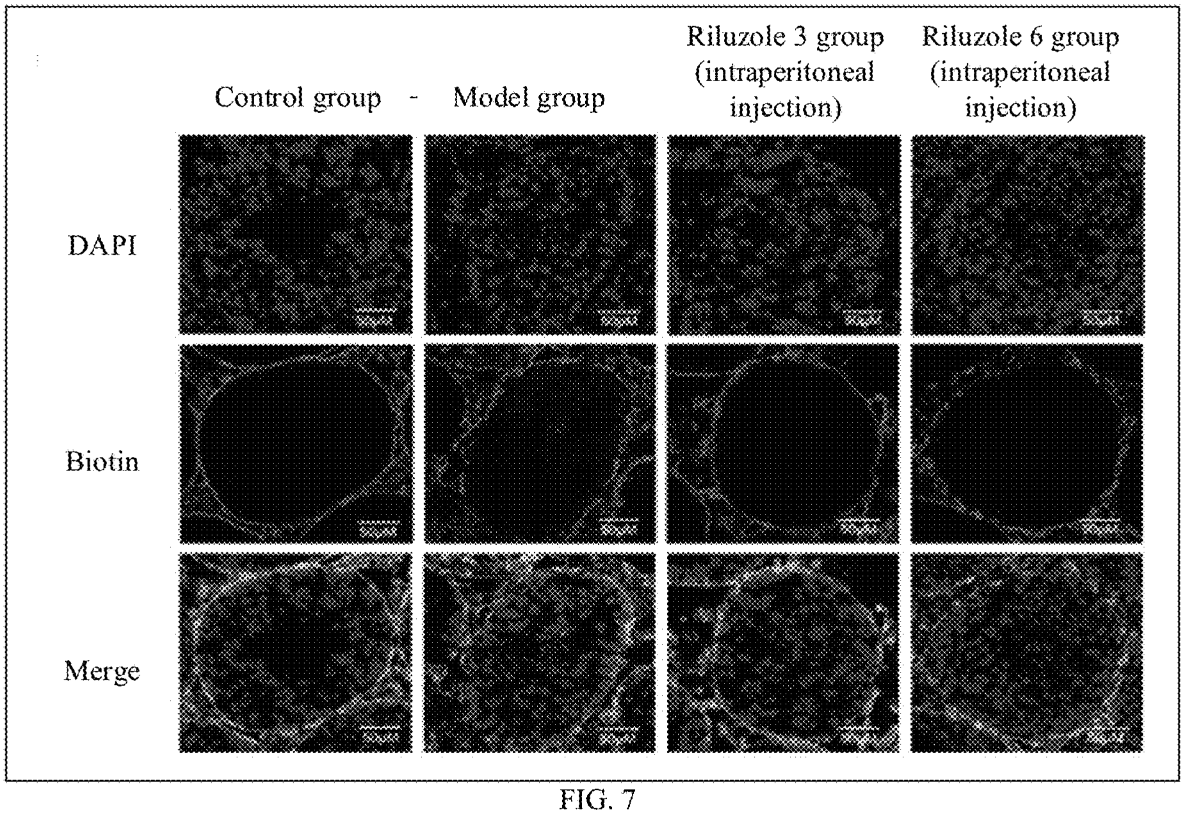
FIG. 7 is a diagram showing an integrity of blood-testis barrier (BTB) in the testes of the busulfan-modeled mice after intraperitoneal administration of riluzole (3 mg/kg, 6 mg/kg) for seven consecutive days detected by biotin.

Because the blood-testis barrier plays an important role in regulating the proliferation and differentiation of spermatogonium, the integrity of the blood-testis barrier in the model mice administrated with the busulfan is detected by biotin labeling. The results show that in the model group, the biotin is diffused into the seminiferous tubule lumen due to the destruction of the blood-testis barrier. Surprisingly, after the riluzole is administered, the blood-testis barrier of the mouse testis is more complete (FIG. 7).

Those skilled in the art should understand that although the disclosure has been specifically described with reference to the above embodiments, it is not limited to these specific embodiments. Based on the methods and technical solutions taught in the disclosure, those skilled in the art can make appropriate modifications or improvements without departing from the spirit of the disclosure, and the resulting equivalent embodiments are within the scope of the disclosure.

What is claimed is:

1. A method of treating oligospermia with one of riluzole and a prodrug thereof, comprising:

administering to a subject with oligospermia a drug comprising one of the riluzole and the prodrug thereof.

2. The method as claimed in claim 1, the subject is one of male vertebrates and rodents.

3. The method as claimed in claim 2, the subject is a mammal.

4. The method as claimed in claim 3, the subject is a human.

5. The method as claimed in claim 1, wherein the drug is suitable for one of oral, sublingual, nasal, local, pulmonary, percutaneous, and parenteral administrations.

6. The method as claimed in claim 5, wherein the drug is suitable for one of the oral administration and intraperitoneal injection administration.

7. The method as claimed in claim 6, wherein the drug is in a form of one of tablets, coated tablets, dragee, pills, cachet, gelatin capsules, solutions, emulsions, suspensions, suppositories, ointments, aerosols and injections.

8. The method as claimed in claim 1, wherein the oligospermia is caused by at least one selected from the group consisting of testicular injury, cancer therapy comprising chemotherapy with busulfan and radiotherapy, severe systemic diseases, malnutrition, drug abuse, anti-psychotherapy and genetic problems.

9. The method as claimed in claim 1, wherein the prodrug is one of a compound represented by the following chemical structural formula:

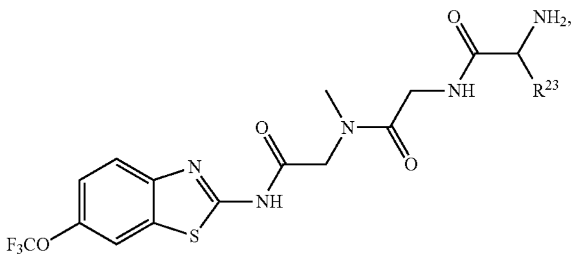

and a pharmaceutically acceptable salt of the compound;

where $R^{23}$ is selected from the group consisting of H, $CH_3$, $CH_2CH_3$, $CH_2CH_2CH_3$, $CH_2CCH$, $CH(CH_3)_2$, $CH_2CH(CH_3)_2$, $CH(CH_3)CH_2CH_3$, $CH_2OH$, $CH_2OCH_2Ph$, $CH_2CH_2OCH_2Ph$, $CH(OH)CH_3$, $CH_2Ph$, $CH_2$(cyclohexyl), $CH_2$(4-OH-Ph), $(CH_2)_4$ $NH_2$, $(CH_2)_3$ $NHC(NH_2)NH$, $CH_2$(3-indole), $CH_2$(5-imidazole), $CH_2CO_2H$, $CH_2CH_2CO_2H$, $CH_2CONH_2$ and $CH_2CH_2CONH_2$, and the Ph represents phenyl.

10. The method as claimed in claim 2, wherein the prodrug is a compound represented by the following chemical structural formula:

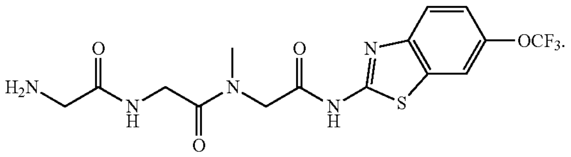 [SMILES: CN(CC(=O)Nc1nc2ccc(OC(F)(F)F)cc2s1)C(=O)CNC(=O)CN]

11. The method as claimed in claim 1, comprising:

treating the oligospermia by administering one of the riluzole and the prodrug thereof in combination with one of another drug and a therapy.

12. The method as claimed in claim 11, wherein one of the another drug and the therapy is one or a combination selected from the group consisting of vitamins, antioxidant, human chorionic gonadotropin (hCG), recombinant human follicle-stimulating hormone (rFSH), gonadotropin-releasing hormone (GnRH), and selective estrogen receptor modulators.

13. The method as claimed in claim 1, comprising:

administering to the subject with oligospermia an effective amount of riluzole intraperitoneally at a dose of 3 milligrams per kilogram (mg/kg) of body weight per day.

14. The method as claimed in claim 1, comprising:

administering to the subject with oligospermia an effective amount of riluzole orally at a dose of 5 mg/kg of body weight per day.

* * * * *